United States Patent
Lee et al.

(10) Patent No.: US 9,157,086 B2
(45) Date of Patent: Oct. 13, 2015

(54) **SHUTTLE VECTORS FOR *CORYNEBACTERIUM* AND *ESCHERICHIA COLI***

(71) Applicant: Samsung Electronics Co., Ltd, Suwon-si, Gyeonggi-do (KR)

(72) Inventors: Woo-yong Lee, Hwaseong-si (KR); Young-min Lee, Suwon-si (KR); Jae-chan Park, Yongin-si (KR); Jin-hwan Park, Suwon-si (KR); Yeo-ju Song, Incheon (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/163,743

(22) Filed: Jan. 24, 2014

(65) Prior Publication Data

US 2014/0212886 A1    Jul. 31, 2014

(30) Foreign Application Priority Data

Jan. 25, 2013  (KR) .................. 10-2013-0008745

(51) Int. Cl.
  *C12N 15/77*  (2006.01)
  *C12N 15/70*  (2006.01)
(52) U.S. Cl.
  CPC ............... *C12N 15/77* (2013.01); *C12N 15/70* (2013.01)

(58) Field of Classification Search
  None
  See application file for complete search history.

(56) References Cited

U.S. PATENT DOCUMENTS 5,643,790 A     7/1997  Morinaga et al.
2010/0261256 A1  10/2010  Rah et al.

FOREIGN PATENT DOCUMENTS

JP     07-039383 A     2/1995
KR   1992-0007401 B1   8/1992

OTHER PUBLICATIONS

Noh et al., Kor. Jour. Microbiol., 1991, vol. 29, pp. 149-154.*
Noh et al., "Effects of Cloned Genes on the Stability of Shuttle Vectors between *Escherichia coli* and *Corynebacterium glutamicum*", Korean Journal Microbiology 29(3): 149-154 (Jul. 1991).

* cited by examiner

Primary Examiner — Michele K Joike
Assistant Examiner — Mindy G Brown
(74) Attorney, Agent, or Firm — Leydig, Voit & Mayer, Ltd.

(57) ABSTRACT

A vector that allows for easy accomplishment of a variety of cloning, and use of the vector for measurement of the transcription-inducing activity of a promoter or production of a desired gene product in *Corynebacterium*.

14 Claims, 5 Drawing Sheets

SEQUENCE LISTING

```
<160> NUMBER OF SEQ ID NOS: 6

<210> SEQ ID NO 1
<211> LENGTH: 4604
<212> TYPE: DNA
<213> ORGANISM: Artificial Sequence
<220> FEATURE:
<223> OTHER INFORMATION: Synthetic (pGSK+_backbone)

<400> SEQUENCE: 1
aacaacaaga cccatcatag tttgccccg cgacattgac cataaattca tcgcacaaaa      60
tatcgaacgg ggtttatgcc gcttttagtg ggtgcgaaga atagtctgct cattacccgc    120
gaacaccgcc gcattcagat cacgcttagt agcgtcccca tgagtaggca gaaccgcgtc    180
caagtccaca tcatccataa cgatcatgca cggggtggaa tccacaccca gacttgccag    240
cacctcatta gcgacacgtt gcgcagcggc cacgtcctta gccttatcca cgcaatctag    300
gacgtactgc ctaaccgcga aatcagactg aatcagtttc caatcatcgg gcttcaccaa    360
agcaacagca acgcggttg attcgacccg ttccggtgct tccagaccgg cgagcttgta    420
cagttcttct tccatttcac gacgtacatc agcgtctatg taatcaatgc ccaaagcacg    480
cttagcccca cgtgaccagg acgaacgcag gtttttagaa ccaacctcat actcacgcca    540
ccgagccacc aaaacagcgt ccatatcctc gccggcgtcg ctttgatcgg ccaacatatc    600
caacatctga aacggcgtgt acgacccctt agacgcggtt ttagtagcgg agccagtcag    660
ttcctgagac atgcccttag cgaggtaggt tgccattttc gcagcgtctc cacccaggt    720 agacacctga tcaagtttga ccccgtgctc acgcagtggc gcgtccatac cggccttaac    780
cacaccagca gaccagcggg aaaacatgga atcctcaaac gccttgagtt catcgtcaga    840
cagtggacga tccaagaaca acagcatgtt gcggtgcaag tgccaaccgt tcgcccaaga    900
gtctgtgacc tcatagtcac tataggtgtg ctccaccccg taccgtgcac gttctttctt    960
ccactgagat gttttcacca tcgaagagta cgcagtctta atacccgctt caacctgcgc   1020
aaatgactgt gagcggttgt gtcgaacagt gcccacaaac atcatgagcg cgccaccgc    1080 cgccaagtga ttcttagtag caatagccag ctcaatgcgg cgttcgccca tgacttccaa   1140
ttcagccaga ggtgaccccc agcgagagtg agagttttgc agaccctcaa actgcgaagc   1200
accgttagac gaccaggaca ccgcaacagc ttcgtccctg cgccacctat ggcaccccgc   1260
```

```
cagagcctta ctattggtga tcttgtacat gacgttttgc ctacgccacg ccctagcgcg    1320
agtgacctta gaaccctcat tgacctgcgg ttccttagag gtgttcactt ctatttcagt    1380
gttacctaga cccgatgttg tgcggggttg cgcagtgcga gtttgtgcgg gtgttgtgcc    1440
cgttgtctta gctagtgcta tggttgtcaa ttgaaacccc ttcgggttat gtggcccccg    1500
tgcatatgag ttggtagctc gcacgggggt ttgtcttgtc taggaactat taattttag    1560 tggtgtttgg tggccgccta gcttggctat gcgtgccagc ttacccgtac tcaatgttaa    1620
agatttgcat cgacatggga gggttacgtg tccgatacct agggggggta tccgcgacta    1680
ggtgccccgg tgctcactgt ctgtaccggc ggggcaagcc ccacaccccg catgacagg    1740 gtggctccgc cccctgcacc cccagcaatc tgcatgtaca tgttttacac attagcacga    1800
catgactgca tgtgcatgca ctgcatgcag actaggtaaa tatgagtatg tacgactagt    1860
aacaggagca ctgcacataa tgaatgagtt gcaggacaat gtttgctacg catgcgcatg    1920
acatatcgca ggaaagctac tagagtctta aagcatggca accaaggcac agctagaaca    1980
gcaactacaa gaagctcaac aggcactaca ggcgcagcaa gcgcaggcac aagccaccat    2040
cgaagcacta aagcgcagg caaaggctaa gcccgtcgtg gtcaccgcac gcgttccttt    2100
ggcactacgt gaggacatga agcgcgcagg catgcagaac ggtgaaaacc tccaagagtt    2160
catgatcgcc gcgtttaccg agcggctaga aaagctcacc accaccgaca acgaggaaaa    2220
caatgtctaa cccactagtt ctctttgccc accgtgaccc ggtaaatgac gtgacgttcg    2280
agtgcattga gcacgccacc tacgacacac tttcacacgc taaagaccag atcaccgccc    2340
aaatgcaagc cctagacgaa gaagccgccc tactgcccta atgggtgttt catgggtgtt    2400
tccctagtgt ttcatggtgt tttcacctaa gctagggaat tgcgcgagaa gtctcgcaaa    2460
aatcagcaac ccccggaacc acacagttca cgggggttct tctatgccag aaatcagaaa    2520
ggggaaccag tgaacgaccc cgaatattgg atcacagcgc agcaggtcgc cgcccgcgta    2580
gctctcaccc cggccaccat taaaaagtgg gcaaacgagg gaaaaatcac cgcatacaag    2640
atcggcaagt ccgtccgatt caaagcatca gacgtagaca agctagggg gggggggcgc    2700 tgaggtctgc ctcgtgaaga aggtgttgct gactcatacc aggcctgaat cgccccatca    2760
tccagccaga aagtgaggga gccacggttg atgagagctt tgttgtaggt ggaccagttg    2820
gtgattttga acttttgctt tgccacggaa cggtctgcgt tgtcgggaag atgcgtgatc    2880
tgatccttca actcagcaaa agttcgattt attcaacaaa gccgccgtcc cgtcaagtca    2940
gcgtaatgct ctgccagtgt tacaaccaat taaccaattc tgattagaag aactcgtcaa    3000
gaaggcgata gaaggcgatg cgctgcgaat cgggagcggc gataccgtaa agcacgagga    3060
agcggtcagc ccattcgccg ccaagctctt cagcaatatc acgggtagcc aacgctatgt    3120
cctgatagcg gtccgccaca cccagccggc cacagtcgat gaatccagaa aagcggccat    3180
tttccaccat gatattcggc aagcaggcat cgccatgggt cacgacgaga tcctcgccgt    3240
cgggcatgct cgccttgagc ctggcgaaca gttcggctgg cgcgagcccc tgatgctctt    3300
cgtccagatc atcctgatcg acaagaccgg cttccatccg agtacgtgct cgctcgatgc    3360
gatgtttcgc ttggtggtcg aatgggcagg tagccggatc aagcgtatgc agccgccgca    3420
ttgcatcagc catgatggat actttctcgg caggagcaag gtgagatgac aggagatcct    3480 gcccccggcac ttcgcccaat agcagccagt cccttcccgc ttcagtgaca acgtcgagca    3540
cagctgcgca aggaacgccc gtcgtggcca gccacgatag ccgcgctgcc tcgtcttgca    3600
```

```
gttcattcag ggcaccggac aggtcggtct tgacaaaaag aaccgggcgc ccctgcgctg    3660
acagccggaa cacggcggca tcagagcagc cgattgtctg ttgtgcccag tcatagccga    3720
atagcctctc cacccaagcg gccggagaac ctgcgtgcaa tccatcttgt tcaatcataa    3780
caccccttgt attactgttt atgtaagcag acagtttat tgttcatgat gatatatttt    3840
tatcttgtgc aatgtaacat cagagatttt gagacacaac gtggctttcc ccccccccc    3900 aaaaggatct aggtgaagat ccttttttgat aatctcatga ccaaaatccc ttaacgtgag    3960
ttttcgttcc actgagcgtc agaccccgta gaaaagatca aggatcttc ttgagatcct     4020 ttttttctgc gcgtaatctg ctgcttgcaa acaaaaaaac caccgctacc agcggtggtt    4080
tgtttgccgg atcaagagct accaactctt tttccgaagg taactggctt cagcagagcg    4140
cagataccaa atactgttct tctagtgtag ccgtagttag gccaccactt caagaactct    4200
gtagcaccgc ctacatacct cgctctgcta atcctgttac cagtggctgc tgccagtggc    4260
gataagtcgt gtcttaccgg gttggactca agacgatagt taccggataa ggcgcagcgg    4320
tcgggctgaa cggggggttc gtgcacacag cccagcttgg agcgaacgac ctacaccgaa    4380
ctgagatacc tacagcgtga gctatgagaa agcgccacgc ttcccgaagg gagaaaggcg    4440
gacaggtatc cggtaagcgg cagggtcgga acaggagagc gcacgaggga gcttccaggg    4500
ggaaacgcct ggtatcttta tagtcctgtc gggtttcgcc acctctgact tgagcgtcga    4560
tttttgtgat gctcgtcagg ggggcggagc ctatggaaaa acgc                     4604
```

<210> SEQ ID NO 2
<211> LENGTH: 385
<212> TYPE: DNA
<213> ORGANISM: Artificial Sequence
<220> FEATURE:
<223> OTHER INFORMATION: Synthetic (pGSK+_MCS)

<400> SEQUENCE: 2

```
cctcttcgct attacgccag ctggcgaaag ggggatgtgc tgcaaggcga ttaagttggg     60
taacgccagg gttttcccag tcacgacgtt gtaaaacgac ggccagtgaa ttgtaatacg    120
actcactata gggcgaattg ggtaccgggc cccccctcga ggtcgacggt atcgataagc    180
ttgatatcga attcctgcag cccggggggat ccactagttc tagagcggcc gccaccgcgg    240
tggagctcca gcttttgttc cctttagtga gggttaattt cgagcttggc gtaatcatgg    300
tcatagctgt ttcctgtgtg aaattgttat ccgctcacaa ttccacacaa catacgagcc    360
ggaagcataa agtgtaaagc ctggg                                          385
```

<210> SEQ ID NO 3
<211> LENGTH: 4990
<212> TYPE: DNA
<213> ORGANISM: Artificial Sequence
<220> FEATURE:
<223> OTHER INFORMATION: Synthetic (pGSK+)

<400> SEQUENCE: 3

```
ttgagatcct ttttttctgc gcgtaatctg ctgcttgcaa acaaaaaaac caccgctacc     60
agcggtggtt tgtttgccgg atcaagagct accaactctt tttccgaagg taactggctt    120
cagcagagcg cagataccaa atactgttct tctagtgtag ccgtagttag gccaccactt    180
caagaactct gtagcaccgc ctacatacct cgctctgcta atcctgttac cagtggctgc    240
tgccagtggc gataagtcgt gtcttaccgg gttggactca agacgatagt taccggataa    300
ggcgcagcgg tcgggctgaa cggggggttc gtgcacacag cccagcttgg agcgaacgac    360
```

```
ctacaccgaa ctgagatacc tacagcgtga gctatgagaa agcgccacgc ttcccgaagg    420
gagaaaggcg gacaggtatc cggtaagcgg cagggtcgga acaggagagc gcacgaggga    480
gcttccaggg ggaaacgcct ggtatcttta tagtcctgtc gggtttcgcc acctctgact    540
tgagcgtcga tttttgtgat gctcgtcagg ggggcggagc ctatggaaaa acgcccctct    600
tcgctattac gccagctggc gaaaggggga tgtgctgcaa ggcgattaag ttgggtaacg    660
ccagggtttt cccagtcacg acgttgtaaa acgacggcca gtgaattgta atacgactca    720
ctatagggcg aattgggtac cgggcccccc ctcgaggtcg acggtatcga taagcttgat    780
atcgaattcc tgcagcccgg gggatccact agttctagag cggccgccac cgcggtggag    840
ctccagcttt tgttcccttt agtgagggtt aatttcgagc ttggcgtaat catggtcata    900
gctgtttcct gtgtgaaatt gttatccgct cacaattcca cacaacatac gagccggaag    960
cataaagtgt aaagcctggg aacaacaaga cccatcatag tttgccccg cgacattgac    1020 cataaattca tcgcacaaaa tatcgaacgg ggtttatgcc gcttttagtg ggtgcgaaga    1080
atagtctgct cattacccgc gaacaccgcc gcattcagat cacgcttagt agcgtcccca    1140
tgagtaggca gaaccgcgtc caagtccaca tcatccataa cgatcatgca cggggtggaa    1200
tccacaccca gacttgccag cacctcatta gcgacacgtt gcgcagcggc cacgtcctta    1260
gccttatcca cgcaatctag gacgtactgc ctaaccgcga aatcagactg aatcagtttc    1320
caatcatcgg gcttcaccaa agcaacagca acgcgggttg attcgacccg ttccggtgct    1380
tccagaccgg cgagcttgta cagttcttct tccatttcac gacgtacatc agcgtctatg    1440
taatcaatgc ccaaagcacg cttagcccca cgtgaccagg acgaacgcag ttttttagaa    1500
ccaacctcat actcacgcca ccgagccacc aaaacagcgt ccatatcctc gccggcgtcg    1560
ctttgatcgg ccaacatatc caacatctga aacggcgtgt acgacccctt agacgcggtt    1620
ttagtagcgg agccagtcag ttcctgagac atgcccttag cgaggtaggt tgccattttc    1680
gcagcgtctc caccccaggt agacacctga tcaagtttga ccccgtgctc acgcagtggc    1740
gcgtccatac cggccttaac cacaccagca gaccagcggg aaaacatgga atcctcaaac    1800
gccttgagtt catcgtcaga cagtggacga tccaagaaca acagcatgtt gcggtgcaag    1860
tgccaaccgt tcgcccaaga gtctgtgacc tcatagtcac tataggtgtg ctccaccccg    1920
taccgtgcac gttctttctt ccactgagat gttttcacca tcgaagagta cgcagtctta    1980
atacccgctt caacctgcgc aaatgactgt gagcggttgt gtcgaacagt gcccacaaac    2040
atcatgagcg cgccacccgc cgccaagtga ttcttagtag caatagccag ctcaatgcgg    2100
cgttcgccca tgacttccaa ttcagccaga ggtgaccccc agcgagagtg agattttgc     2160 agaccctcaa actgcgaagc accgttagac gaccaggaca ccgcaacagc ttcgtccctg    2220
cgccacctat ggcaccccgc cagagcctta ctattggtga tcttgtacat gacgttttgc    2280
ctacgccacg ccctagcgcg agtgacctta gaaccctcat tgacctgcgg ttccttagag    2340
gtgttcactt ctatttcagt gttacctaga cccgatgttg tgcggggttg cgcagtgcga    2400
gtttgtgcgg gtgttgtgcc cgttgtctta gctagtgcta tggttgtcaa ttgaaacccc    2460
ttcgggttat gtggccccg tgcatatgag ttggtagctc gcacggggt ttgtcttgtc     2520 taggaactat taattttag tggtgttgg tggccgccta gcttggctat gcgtgccagc     2580
ttacccgtac tcaatgttaa agatttgcat cgacatggga gggttacgtg tccgatacct    2640
agggggggta tccgcgacta ggtgcccgg tgctcactgt ctgtaccggc ggggcaagcc     2700
```

```
ccacacccccg catggacagg gtggctccgc ccccctgcacc cccagcaatc tgcatgtaca    2760
tgttttacac attagcacga catgactgca tgtgcatgca ctgcatgcag actaggtaaa    2820
tatgagtatg tacgactagt aacaggagca ctgcacataa tgaatgagtt gcaggacaat    2880
gtttgctacg catgcgcatg acatatcgca ggaaagctac tagagtctta aagcatggca    2940
accaaggcac agctagaaca gcaactacaa gaagctcaac aggcactaca ggcgcagcaa    3000
gcgcaggcac aagccaccat cgaagcacta gaagcgcagg caaaggctaa gcccgtcgtg    3060
gtcaccgcac gcgttccttt ggcactacgt gaggacatga agcgcgcagg catgcagaac    3120
ggtgaaaacc tccaagagtt catgatcgcc gcgtttaccg agcggctaga aaagctcacc    3180
accaccgaca acgaggaaaa caatgtctaa cccactagtt ctctttgccc accgtgaccc    3240
ggtaaatgac gtgacgttcg agtgcattga gcacgccacc tacgacacac tttcacacgc    3300
taaagaccag atcaccgccc aaatgcaagc cctagacgaa gaagccgccc tactgcccta    3360
atgggtgttt catgggtgtt tccctagtgt tcatggtgtg tttcacctaa gctagggaat    3420
tgcgcgagaa gtctcgcaaa aatcagcaac ccccggaacc acacagttca cgggggttct    3480
tctatgccag aaatcagaaa ggggaaccag tgaacgaccc cgaatattgg atcacagcgc    3540
agcaggtcgc cgcccgcgta gctctcaccc cggccaccat taaaaagtgg gcaaacgagg    3600
gaaaaatcac cgcatacaag atcggcaagt ccgtccgatt caaagcatca gacgtagaca    3660
agctaggggg ggggggcgc tgaggtctgc ctcgtgaaga aggtgttgct gactcatacc    3720
aggcctgaat cgccccatca tccagccaga aagtgaggga gccacggttg atgagagctt    3780
tgttgtaggt ggaccagttg gtgattttga acttttgctt tgccacggaa cggtctgcgt    3840
tgtcgggaag atgcgtgatc tgatccttca actcagcaaa agttcgattt attcaacaaa    3900
gccgccgtcc cgtcaagtca gcgtaatgct ctgccagtgt tacaaccaat taaccaattc    3960
tgattagaag aactcgtcaa gaaggcgata gaaggcgatg cgctgcgaat cgggagcggc    4020
gataccgtaa agcacgagga agcggtcagc ccattcgccg ccaagctctt cagcaatatc    4080
acgggtagcc aacgctatgt cctgatagcg gtccgccaca cccagccggc cacagtcgat    4140
gaatccagaa aagcggccat tttccaccat gatattcggc aagcaggcat cgccatgggt    4200
cacgacgaga tcctcgccgt cgggcatgct cgccttgagc ctggcgaaca gttcggctgg    4260
cgcgagcccc tgatgctctt cgtccagatc atcctgatcg acaagaccgg cttccatccg    4320
agtacgtgct cgctcgatgc gatgtttcgc ttggtggtcg aatgggcagg tagccggatc    4380
aagcgtatgc agccgccgca ttgcatcagc catgatggat actttctcgg caggagcaag    4440
gtgagatgac aggagatcct gccccggcac ttcgcccaat agcagccagt cccttcccgc    4500
ttcagtgaca acgtcgagca cagctgcgca aggaacgccc gtcgtggcca gccacgatag    4560
ccgcgctgcc tcgtcttgca gttcattcag ggcaccggac aggtcggtct tgacaaaaag    4620
aaccgggcgc ccctgcgctg acagccgaa cacggcggca tcagagcagc cgattgtctg    4680
ttgtgcccag tcatagccga atagcctctc cacccaagcg gccggagaac ctgcgtgcaa    4740
tccatcttgt tcaatcataa cacccccttgt attactgttt atgtaagcag acagttttat    4800
tgttcatgat gatatatttt tatcttgtgc aatgtaacat cagagatttt gagacacaac    4860
gtggctttcc cccccccccc aaaaggatct aggtgaagat cctttttgat aatctcatga    4920
ccaaaatccc ttaacgtgag ttttcgttcc actgagcgtc agacccgta gaaaagatca    4980
aaggatcttc                                                           4990
```

```
<210> SEQ ID NO 4
<211> LENGTH: 6314
<212> TYPE: DNA
<213> ORGANISM: Artificial Sequence
<220> FEATURE:
<223> OTHER INFORMATION: Synthetic (pGPS1)

<400> SEQUENCE: 4
ttgagatcct tttttctgc gcgtaatctg ctgcttgcaa acaaaaaaac caccgctacc      60
agcggtggtt tgtttgccgg atcaagagct accaactctt tttccgaagg taactggctt    120
cagcagagcg cagataccaa atactgttct tctagtgtag ccgtagttag gccaccactt    180
caagaactct gtagcaccgc ctacatacct cgctctgcta atcctgttac cagtggctgc    240
tgccagtggc gataagtcgt gtcttaccgg gttggactca agacgatagt taccggataa    300
ggcgcagcgg tcgggctgaa cggggggttc gtgcacacag cccagcttgg agcgaacgac    360
ctacaccgaa ctgagatacc tacagcgtga gctatgagaa agcgccacgc ttcccgaagg    420
gagaaaggcg gacaggtatc cggtaagcgg cagggtcgga acaggagagc gcacgaggga    480
gcttccaggg ggaaacgcct ggtatcttta tagtcctgtc gggtttcgcc acctctgact    540
tgagcgtcga ttttttgtgat gctcgtcagg ggggcggagc ctatggaaaa acgccctct    600 tcgctattac gccagctggc gaaagggggga tgtgctgcaa ggcgattaag ttgggtaacg    660
ccagggtttt cccagtcacg acgttgtaaa acgacggcca gtgaattgta atacgactca    720
ctatagggcg aattgggtac cgggcccccc ctcgaggtcg acggtatcga tggagaaaaa    780
aatcactgga tataccaccg ttgatatatc ccaatggcat cgtaaagaac attttgaggc    840
atttcagtca gttgctcaat gtacctataa ccagaccgtt cagctggata ttacggcctt    900
tttaaagacc gtaaagaaaa ataagcacaa gttttatccg ccttattc acattcttgc     960 ccgcctgatg aatgctcatc cggagttccg tatggcaatg aaagacggtg agctggtgat   1020
atgggatagt gttcacccct tgttacaccg ttttccatgag caaactgaaa cgttttcatc   1080
gctctggagt gaataccacg acgatttccg gcagtttcta cacatatatt cgcaagatgt   1140
ggcgtgttac ggtgaaaacc tggcctattt ccctaaaggg tttattgaga atatgttttt   1200
cgtctcagcc aatccctggg tgagtttcac cagttttgat ttaaacgtgg ccaatatgga   1260
caacttcttc gcccccgttt tcaccatggg caaatattat acgcaaggcg acaaggtgct   1320
gatgccgctg gcgattcagg ttcatcatgc cgtttgtgat ggcttccatg tcggcagaat   1380
gcttaatgaa ttacaacagt actgcgatga gtggcagggc ggggcgtaat tttttttaagg   1440 cagttattgg tgcccttaaa cgcctggttg ctacgcctga ataagtgata ataagcggat   1500
gaatggcaga aattcgtcga ggcggcacct cgctaacgga ttcaccactc caagaattgg   1560
agccaatcaa ttcttgcgga gaactgtgaa tgcgcaaacc aacccttggc agaacatatc   1620
catcgcgtcc gccatctcca gcagccgcac gcggcgcatc tcggctgttt tggcggatga   1680
gagaagattt tcagcctgat acagattaaa tcagaacgca gaagcggtct gataaaacag   1740
aatttgcctg gcggcagtag cgcggtggtc ccacctgacc ccatgccgaa ctcagaagtg   1800
aaacgccgta gcgccgatgg tagtgtgggg tctccccatg cgagagtagg gaactgccag   1860
gcatcaaata aaacgaaagg ctcagtcgaa agactgggcc tttcgtttta tctgttgttt   1920
gtcggtgaac gctctcctga gtaggacaaa tccgccggga gcggatttga acgttgcgaa   1980
gcaacgcccc ggagggtggc gggcaggacg cccgccataa actgccaggc atcaaattaa   2040
gcagaaggcc atcctgacgg atggcctttt tgcgtttcta caaactcttc ctgtcgtcat   2100
```

```
atctacaagc catcccccca cagatacggt aaactagcct cgttttgca tcaggaaagc    2160 agagctccag cttttgttcc ctttagtgag ggttaatttc gagcttggcg taatcatggt    2220
catagctgtt tcctgtgtga aattgttatc cgctcacaat tccacacaac atacgagccg    2280
gaagcataaa gtgtaaagcc tgggaacaac aagaccatc atagtttgcc cccgcgacat     2340
tgaccataaa ttcatcgcac aaaatatcga acggggttta tgccgctttt agtgggtgcg    2400
aagaatagtc tgctcattac ccgcgaacac cgccgcattc agatcacgct tagtagcgtc    2460
cccatgagta ggcagaaccg cgtccaagtc cacatcatcc ataacgatca tgcacggggt    2520
ggaatccaca cccagacttg ccagcacctc attagcgaca cgttgcgcag cggccacgtc    2580
cttagcctta tccacgcaat ctaggacgta ctgcctaacc gcgaaatcag actgaatcag    2640
tttccaatca tcgggcttca ccaaagcaac agcaacgcgg gttgattcga cccgttccgg    2700
tgcttccaga ccggcgagct tgtacagttc ttcttccatt tcacgacgta catcagcgtc    2760
tatgtaatca atgcccaaag cacgcttagc cccacgtgac caggacgaac gcaggttttt    2820
agaaccaacc tcatactcac gccaccgagc caccaaaaca gcgtccatat cctgccggc    2880 gtcgctttga tcggccaaca tatccaacat ctgaaacggc gtgtacgacc ccttagacgc    2940
ggttttagta gcggagccag tcagttcctg agacatgccc ttagcgaggt aggttgccat    3000
tttcgcagcg tctccacccc aggtagacac ctgatcaagt ttgacccgt gctcacgcag      3060 tggcgcgtcc ataccggcct taaccacacc agcagaccag cggaaaaca tggaatcctc     3120 aaacgccttg agttcatcgt cagacagtgg acgatccaag aacaacagca tgttgcggtg    3180
caagtgccaa ccgttcgccc aagagtctgt gacctcatag tcactatagg tgtgctccac    3240
cccgtaccgt gcacgttctt tcttccactg agatgttttc accatcgaag agtacgcagt    3300
cttaataccc gcttcaacct gcgcaaatga ctgtgagcgg ttgtgtcgaa cagtgccac     3360 aaacatcatg agcgcgccac ccgccgccaa gtgattctta gtagcaatag ccagctcaat    3420
gcggcgttcg cccatgactt ccaattcagc cagaggtgac ccccagcgag agtgagagtt    3480
ttgcagaccc tcaaactgcg aagcaccgtt agacgaccag gacaccgcaa cagcttcgtc    3540
cctgcgccac ctatggcacc ccgccagagc cttactattg gtgatcttgt acatgacgtt    3600
ttgcctacgc cacgccctag cgcgagtgac cttagaaccc tcattgacct gcggttcctt    3660
agaggtgttc acttctatt cagtgttacc tagacccgat gttgtgcggg gttgcgcagt     3720
gcgagtttgt gcggtgttg tgcccgttgt cttagctagt gctatggttg tcaattgaaa     3780
ccccttcggg ttatgtggcc cccgtgcata tgagttggta gctcgcacgg gggtttgtct    3840
tgtctaggaa ctattaattt ttagtggtgt ttggtggccg cctagcttgg ctatgcgtgc    3900
cagcttaccc gtactcaatg ttaaagattt gcatcgacat gggagggtta cgtgtccgat    3960
acctaggggg ggtatccgcg actaggtgcc ccggtgctca ctgtctgtac cggcggggca    4020
agccccacac cccgcatgga cagggtggct ccgcccctg cacccccagc aatctgcatg     4080
tacatgtttt acacattagc acgacatgac tgcatgtgca tgcactgcat gcagactagg    4140
taaatatgag tatgtacgac tagtaacagg agcactgcac ataatgaatg agttgcagga    4200
caatgtttgc tacgcatgcg catgacatat cgcaggaaag ctactagagt cttaaagcat    4260
ggcaaccaag gcacagctag aacagcaact acaagaagct caacaggcac tacaggcgca    4320
gcaagcgcag gcacaagcca ccatcgaagc actagaagcg caggcaaagg ctaagcccgt    4380
cgtggtcacc gcacgcgttc ctttggcact acgtgaggac atgaagcgcg caggcatgca    4440
gaacggtgaa aacctccaag agttcatgat cgccgcgttt accgagcggc tagaaaagct    4500
```

```
caccaccacc gacaacgagg aaaacaatgt ctaacccact agttctcttt gcccaccgtg    4560
acccggtaaa tgacgtgacg ttcgagtgca ttgagcacgc cacctacgac acactttcac    4620
acgctaaaga ccagatcacc gcccaaatgc aagccctaga cgaagaagcc gccctactgc    4680
cctaatgggt gtttcatggg tgtttcccta gtgtttcatg gtgttttcac ctaagctagg    4740
gaattgcgcg agaagtctcg caaaaatcag caaccccggg aaccacacag ttcacgggggg   4800 ttcttctatg ccagaaatca gaaaggggaa ccagtgaacg accccgaata ttggatcaca    4860
gcgcagcagg tcgccgcccg cgtagctctc accccggcca ccattaaaaa gtgggcaaac    4920
gagggaaaaa tcaccgcata caagatcggc aagtccgtcc gattcaaagc atcagacgta    4980
gacaagctag ggggggggg gcgctgaggt ctgcctcgtg aagaaggtgt tgctgactca     5040
taccaggcct gaatcgcccc atcatccagc cagaaagtga gggagccacg gttgatgaga    5100
gctttgttgt aggtggacca gttggtgatt ttgaactttt gctttgccac ggaacggtct    5160
gcgttgtcgg gaagatgcgt gatctgatcc ttcaactcag caaaagttcg atttattcaa    5220
caaagccgcc gtcccgtcaa gtcagcgtaa tgctctgcca gtgttacaac caattaacca    5280
attctgatta gaagaactcg tcaagaaggc gatagaaggc gatgcgctgc gaatcgggag    5340
cggcgatacc gtaaagcacg aggaagcggt cagcccattc gccgccaagc tcttcagcaa    5400
tatcacgggt agccaacgct atgtcctgat agcggtccgc cacacccagc cggccacagt    5460
cgatgaatcc agaaaagcgg ccattttcca ccatgatatt cggcaagcag gcatcgccat    5520
gggtcacgac gagatcctcg ccgtcgggca tgctcgcctt gagcctggcg aacagttcgg    5580
ctggcgcgag cccctgatgc tcttcgtcca gatcatcctg atcgacaaga ccggcttcca    5640
tccgagtacg tgctcgctcg atgcgatgtt tcgcttggtg gtcgaatggg caggtagccg    5700
gatcaagcgt atgcagccgc cgcattgcat cagccatgat ggatacttc tcggcaggag    5760 caaggtgaga tgacaggaga tcctgccccg gcacttcgcc caatagcagc cagtcccttc    5820
ccgcttcagt gacaacgtcg agcacagctg cgcaaggaac gcccgtcgtg gccagccacg    5880
atagccgcgc tgcctcgtct tgcagttcat tcagggcacc ggacaggtcg gtcttgacaa    5940
aaagaaccgg gcgcccctgc gctgacagcc ggaacacggc ggcatcagag cagccgattg    6000
tctgttgtgc ccagtcatag ccgaatagcc tctccaccca gcggccgga gaacctgcgt      6060 gcaatccatc ttgttcaatc ataacacccc ttgtattact gtttatgtaa gcagacagtt    6120
ttattgttca tgatgatata tttttatctt gtgcaatgta acatcagaga ttttgagaca    6180
caacgtggct ttccccccccc ccccaaaagg atctaggtga agatccttt tgataatctc     6240 atgaccaaaa tcccttaacg tgagttttcg ttccactgag cgtcagaccc cgtagaaaag    6300
atcaaaggat cttc                                                       6314
```

<210> SEQ ID NO 5
<211> LENGTH: 5342
<212> TYPE: DNA
<213> ORGANISM: Artificial Sequence
<220> FEATURE:
<223> OTHER INFORMATION: Synthetic (pGT1)

<400> SEQUENCE: 5

```
ttgagatcct ttttttctgc gcgtaatctg ctgcttgcaa acaaaaaaac caccgctacc      60
agcggtggtt tgtttgccgg atcaagagct accaactctt tttccgaagg taactggctt     120
cagcagagcg cagataccaa atactgttct tctagtgtag ccgtagttag gccaccactt     180
```

```
caagaactct gtagcaccgc ctacatacct cgctctgcta atcctgttac cagtggctgc    240
tgccagtggc gataagtcgt gtcttaccgg gttggactca agacgatagt taccggataa    300
ggcgcagcgg tcgggctgaa cggggggttc gtgcacacag cccagcttgg agcgaacgac    360
ctacaccgaa ctgagatacc tacagcgtga gctatgagaa agcgccacgc ttcccgaagg    420
gagaaaggcg acaggtatcc ggtaagcgg cagggtcgga acaggagagc gcacgaggga    480
gcttccaggg ggaaacgcct ggtatcttta tagtcctgtc gggtttcgcc acctctgact    540
tgagcgtcga ttttttgtgat gctcgtcagg ggggcggagc ctatggaaaa acgccctct    600 tcgctattac gccagctggc gaaaggggga tgtgctgcaa ggcgattaag ttgggtaacg    660
ccagggtttt cccagtcacg acgttgtaaa acgacggcca gtgaattgta atacgactca    720
ctatagggcg aattgggtac cgggccccc ctcgaggtcg acggtatcga taagcttgat    780
atcgaattcc tgcagcccgg ggatccact agttctagag cggccgccac cgcggtggag    840
ctcatttagc ggatgattct cgttcaactt cggccgaagc cacttcgtct gtcataatga    900
cagggatggt ttcggccgtt tttgcaaata aaacgaaagg ctcagtcgaa agactgggcc    960
tttcgtttta tctgttgttt gtcggtgaac gctctcctga gtaggacaaa tccgccggga   1020
gcggatttga acgttgcgaa gcaacggccc ggagggtggc gggcaggacg cccgccataa   1080
actgccaggc atcaaattaa gcagaaggcc atcctgacgg atggccttt tgcgtttcta   1140 caaactcttc ctgtcgtcat atctacaagc catcccccca cagatacggt agctccagct   1200
tttgttccct ttagtgaggg ttaatttcga gcttggcgta atcatggtca tagctgtttc   1260
ctgtgtgaaa ttgttatccg ctcacaattc cacacaacat acgagccgga agcataaagt   1320
gtaaagcctg gaacaacaa gacccatcat agtttgcccc cgcgacattg accataaatt   1380
catcgcacaa aatatcgaac ggggtttatg ccgcttttag tgggtgcgaa gaatagtctg   1440
ctcattaccc gcgaacaccg ccgcattcag atcacgctta gtagcgtccc catgagtagg   1500
cagaaccgcg tccaagtcca catcatccat aacgatcatg cacggggtgg aatccacacc   1560
cagacttgcc agcacctcat tagcgacacg ttgcgcagcg gccacgtcct tagccttatc   1620
cacgcaatct aggacgtact gcctaaccgc gaaatcagac tgaatcagtt tccaatcatc   1680
gggcttcacc aaagcaacag caacgcgggt tgattcgacc cgttccggtg cttccagacc   1740
ggcgagcttg tacagttctt cttccatttc acgacgtaca tcagcgtcta tgtaatcaat   1800
gcccaaagca cgcttagccc cacgtgacca ggacgaacgc aggttttag aaccaacctc   1860 atactcacgc caccgagcca ccaaaacagc gtccatatcc tcgccggcgt cgcttttgatc   1920 ggccaacata tccaacatct gaaacggcgt gtacgacccc ttagacgcgg ttttagtagc   1980
ggagccagtc agttcctgag acatgccctt agcgaggtag gttgccattt tcgcagcgtc   2040 tccacccag gtagacacct gatcaagttt gaccccgtgc tcacgcagtg gcgcgtccat   2100
accggcctta accacaccag cagaccagcg ggaaaacatg gaatcctcaa acgccttgag   2160
ttcatcgtca gacagtggac gatccaagaa caacagcatg ttgcggtgca agtgccaacc   2220
gttcgcccaa gagtctgtga cctcatagtc actataggtg tgctccaccc cgtaccgtgc   2280 acgttcttc ttccactgag atgttttcac catcgaagag tacgcagtct taatacccgc   2340
ttcaacctgc gcaaatgact gtgagcggtt gtgtcgaaca gtgcccacaa acatcatgag   2400
cgcgccaccc gccgccaagt gattcttagt agcaatagcc agctcaatgc ggcgttcgcc   2460
catgacttcc aattcagcca gaggtgaccc ccagcgagag tgagagtttt gcagaccctc   2520
aaactgcgaa gcaccgttag acgaccagga caccgcaaca gcttcgtccc tgcgccacct   2580
```

```
atggcacccc gccagagcct tactattggt gatcttgtac atgacgtttt gcctacgcca    2640
cgccctagcg cgagtgacct tagaaccctc attgacctgc ggttccttag aggtgttcac    2700
ttctatttca gtgttaccta gacccgatgt tgtgcggggt tgcgcagtgc gagtttgtgc    2760
gggtgttgtg cccgttgtct tagctagtgc tatggttgtc aattgaaacc ccttcgggtt    2820
atgtggcccc cgtgcatatg agttggtagc tcgcacgggg gtttgtcttg tctaggaact    2880
attaattttt agtggtgttt ggtggccgcc tagcttggct atgcgtgcca gcttacccgt    2940
actcaatgtt aaagatttgc atcgacatgg gagggttacg tgtccgatac ctagggggg    3000 tatccgcgac taggtgcccc ggtgctcact gtctgtaccg gcggggcaag ccccacaccc    3060
cgcatggaca gggtggctcc gcccctgca cccccagcaa tctgcatgta catgttttac    3120
acattagcac gacatgactg catgtgcatg cactgcatgc agactaggta aatatgagta    3180
tgtacgacta gtaacaggag cactgcacat aatgaatgag ttgcaggaca atgtttgcta    3240
cgcatgcgca tgacatatcg caggaaagct actagagtct taaagcatgg caaccaaggc    3300
acagctagaa cagcaactac aagaagctca acaggcacta caggcgcagc aagcgcaggc    3360
acaagccacc atcgaagcac tagaagcgca ggcaaaggct aagcccgtcg tggtcaccgc    3420
acgcgttcct ttggcactac gtgaggacat gaagcgcgca ggcatgcaga acggtgaaaa    3480
cctccaagag ttcatgatcg ccgcgtttac cgagcggcta gaaaagctca ccaccaccga    3540
caacgaggaa aacaatgtct aacccactag ttctctttgc ccaccgtgac ccggtaaatg    3600
acgtgacgtt cgagtgcatt gagcacgcca cctacgacac actttcacac gctaaagacc    3660
agatcaccgc ccaaatgcaa gccctagacg aagaagccgc cctactgccc taatgggtgt    3720
ttcatgggtg tttccctagt gtttcatggt gttttcacct aagctaggga attgcgcgag    3780
aagtctcgca aaaatcagca accccggaa ccacacagtt cacgggggtt cttctatgcc    3840
agaaatcaga aagggaacc agtgaacgac cccgaatatt ggatcacagc gcagcaggtc    3900
gccgcccgcg tagctctcac cccggccacc attaaaaagt gggcaaacga gggaaaaatc    3960
accgcataca agatcggcaa gtccgtccga ttcaaagcat cagacgtaga caagctaggg    4020
gggggggggc gctgaggtct gcctcgtgaa gaaggtgttg ctgactcata ccaggcctga    4080
atcgccccat catccagcca gaaagtgagg gagccacggt tgatgagagc tttgttgtag    4140
gtggaccagt tggtgatttt gaacttttgc tttgccacgg aacggtctgc gttgtcggga    4200
agatgcgtga tctgatcctt caactcagca aaagttcgat ttattcaaca aagccgccgt    4260
cccgtcaagt cagcgtaatg ctctgccagt gttacaacca attaaccaat tctgattaga    4320
agaactcgtc aagaaggcga tagaaggcga tgcgctgcga atcgggagcg gcgataccgt    4380
aaagcacgag gaagcggtca gcccattcgc cgccaagctc ttcagcaata tcacgggtag    4440
ccaacgctat gtcctgatag cggtccgcca cacccagccg gccacagtcg atgaatccag    4500
aaaagcggcc attttccacc atgatattcg gcaagcaggc atcgccatgg gtcacgacga    4560
gatcctcgcc gtcgggcatg ctcgccttga gcctggcgaa cagttcggct ggcgcgagcc    4620
cctgatgctc ttcgtccaga tcatcctgat cgacaagacc ggcttccatc cgagtacgtg    4680
ctcgctcgat gcgatgtttc gcttggtggt cgaatgggca ggtagccgga tcaagcgtat    4740
gcagccgccg cattgcatca gccatgatgg atactttctc ggcaggagca aggtgagatg    4800
acaggagatc ctgccccggc acttcgccca atagcagcca gtcccttccc gcttcagtga    4860
caacgtcgag cacagctgcg caaggaacgc ccgtcgtggc cagccacgat agccgcgctg    4920
```

```
cctcgtcttg cagttcattc agggcaccgg acaggtcggt cttgacaaaa agaaccgggc    4980 gccectgcgc tgacagccgg aacacggcgg catcagagca gccgattgtc tgttgtgccc    5040
agtcatagcc gaatagcctc tccacccaag cggccggaga acctgcgtgc aatccatctt    5100
gttcaatcat aacacccctt gtattactgt ttatgtaagc agacagtttt attgttcatg    5160
atgatatatt tttatcttgt gcaatgtaac atcagagatt ttgagacaca acgtggcttt    5220 ccccccccc ccaaaaggat ctaggtgaag atccttttg ataatctcat gaccaaaatc      5280
ccttaacgtg agttttcgtt ccactgagcg tcagacccg tagaaaagat caaaggatct     5340
tc                                                                    5342

<210> SEQ ID NO 6
<211> LENGTH: 5567
<212> TYPE: DNA
<213> ORGANISM: Artificial Sequence
<220> FEATURE:
<223> OTHER INFORMATION: Synthetic (pGSX1)

<400> SEQUENCE: 6
ttgagatcct tttttctgc gcgtaatctg ctgcttgcaa acaaaaaaac caccgctacc       60
agcggtggtt tgtttgccgg atcaagagct accaactctt tttccgaagg taactggctt    120
cagcagagcg cagataccaa atactgttct tctagtgtag ccgtagttag gccaccactt    180
caagaactct gtagcaccgc ctacatacct cgctctgcta atcctgttac cagtggctgc    240
tgccagtggc gataagtcgt gtcttaccgg gttggactca agacgatagt taccggataa    300
ggcgcagcgg tcgggctgaa cggggggttc gtgcacacag cccagcttgg agcgaacgac    360
ctacaccgaa ctgagatacc tacagcgtga gctatgagaa agcgccacgc ttcccgaagg    420
gagaaaggcg gacaggtatc cggtaagcgg cagggtcgga acaggagagc gcacgaggga    480
gcttccaggg ggaaacgcct ggtatcttta tagtcctgtc gggtttcgcc acctctgact    540
tgagcgtcga tttttgtgat gctcgtcagg ggggcggagc ctatggaaaa acgccctct     600 tcgctattac gccagctggc gaaaggggga tgtgctgcaa ggcgattaag ttgggtaacg    660
ccagggtttt cccagtcacg acgttgtaaa acgacggcca gtgaattgta atacgactca    720
ctatagggcg aattgggtac catgattttg catctgctgc gaaatctttg tttccccgct    780
aaagttgagg acaggttgac acggagttga ctcgacgaat tatccaatgt gagtaggttt    840
ggtgcgtgag ttggaaaaat tcgccatact cgcccttggg ttctgtcagc tcaagaattc    900
ttgagtgacc gatgctctga ttgacctaac tgcttgacac attgcatttc ctacaatctt    960
tagaggagac acaacctcga ggtcgacggt atcgataagc ttgatatcga attcctgcag   1020
cccgggggat ccactagttc tagagcggcc gccaccgcgg tggagctcat ttagcggatg   1080
attctcgttc aacttcggcc gaagccactt cgtctgtcat aatgacaggg atggtttcgg   1140 ccgttttgc aaataaaacg aaaggctcag tcgaaagact gggcctttcg ttttatctgt    1200
tgtttgtcgg tgaacgctct cctgagtagg acaaatccgc cgggagcgga tttgaacgtt   1260
gcgaagcaac ggcccggagg gtggcgggca ggacgcccgc cataaactgc caggcatcaa   1320
attaagcaga aggccatcct gacggatggc ctttttgcgt ttctacaaac tcttcctgtc   1380
gtcatatcta caagccatcc ccccacagat acggtagctc cagcttttgt tccctttagt    1440
gagggttaat ttcgagcttg gcgtaatcat ggtcatagct gtttcctgtg tgaaattgtt    1500
atccgctcac aattccacac aacatacgag ccggaagcat aaagtgtaaa gcctgggaac   1560
aacaagaccc atcatagttt gccccgcga cattgaccat aaattcatcg cacaaaatat    1620
```

```
cgaacggggt ttatgccgct tttagtgggt gcgaagaata gtctgctcat tacccgcgaa    1680
caccgccgca ttcagatcac gcttagtagc gtccccatga gtaggcagaa ccgcgtccaa    1740
gtccacatca tccataacga tcatgcacgg ggtggaatcc acacccagac ttgccagcac    1800
ctcattagcg acacgttgcg cagcggccac gtccttagcc ttatccacgc aatctaggac    1860
gtactgccta accgcgaaat cagactgaat cagtttccaa tcatcgggct tcaccaaagc    1920
aacagcaacg cgggttgatt cgacccgttc cggtgcttcc agaccggcga gcttgtacag    1980
ttcttcttcc atttcacgac gtacatcagc gtctatgtaa tcaatgccca agcacgctt     2040
agccccacgt gaccaggacg aacgcaggtt tttagaacca acctcatact cacgccaccg    2100
agccaccaaa acagcgtcca tatcctcgcc ggcgtcgctt tgatcggcca acatatccaa    2160
catctgaaac ggcgtgtacg acccttaga cgcggtttta gtagcggagc cagtcagttc     2220
ctgagacatg cccttagcga ggtaggttgc cattttcgca gcgtctccac cccaggtaga    2280
cacctgatca gtttgaccc cgtgctcacg cagtggcgcg tccataccgg ccttaaccac     2340
accagcagac cagcgggaaa acatggaatc ctcaaacgcc ttgagttcat cgtcagacag    2400
tggacgatcc aagaacaaca gcatgttgcg gtgcaagtgc caaccgttcg cccaagagtc    2460
tgtgacctca tagtcactat aggtgtgctc cacccgtac cgtgcacgtt ctttcttcca     2520
ctgagatgtt ttcaccatcg aagagtacgc agtcttaata cccgcttcaa cctgcgcaaa    2580
tgactgtgag cggttgtgtc gaacagtgcc cacaaacatc atgagcgcgc cacccgccgc    2640
caagtgattc ttagtagcaa tagccagctc aatgcggcgt tcgcccatga cttccaattc    2700
agccagaggt gaccccagc gagagtgaga gttttgcaga ccctcaaact gcgaagcacc     2760
gttagacgac caggacaccg caacagcttc gtccctgcgc cacctatggc accccgccag    2820
agccttacta ttggtgatct tgtacatgac gttttgccta cgccacgccc tagcgcgagt    2880
gaccttagaa ccctcattga cctgcggttc cttagaggtg ttcacttcta tttcagtgtt    2940
acctagaccc gatgttgtgc ggggttgcgc agtgcgagtt tgtgcgggtg ttgtgcccgt    3000
tgtcttagct agtgctatgg ttgtcaattg aaacccccttc gggttatgtg gccccgtgc    3060
atatgagttg gtagctcgca cggggggtttg tcttgtctag gaactattaa ttttagtgg    3120
tgtttggtgg ccgcctagct tggctatgcg tgccagctta cccgtactca atgttaaaga    3180
tttgcatcga catgggaggg ttacgtgtcc gatacctagg ggggtatcc gcgactaggt    3240
gccccggtgc tcactgtctg taccggcggg gcaagcccca caccccgcat ggacagggtg    3300
gctccgcccc ctgcacccccc agcaatctgc atgtacatgt tttacacatt agcacgacat    3360
gactgcatgt gcatgcactg catgcagact aggtaaatat gagtatgtac gactagtaac    3420
aggagcactg cacataatga atgagttgca ggacaatgtt tgctacgcat gcgcatgaca    3480
tatcgcagga aagctactag agtcttaaag catggcaacc aaggcacagc tagaacagca    3540
actacaagaa gctcaacagg cactacaggc gcagcaagcg caggcacaag ccaccatcga    3600
agcactagaa gcgcaggcaa aggctaagcc cgtcgtggtc accgcacgcg ttccttttggc   3660
actacgtgag gacatgaagc gcgcaggcat gcagaacggt gaaaacctcc aagagttcat    3720
gatcgccgcg tttaccgagc ggctagaaaa gctcaccacc accgacaacg aggaaaacaa    3780
tgtctaaccc actagttctc tttgcccacc gtgacccggt aaatgacgtg acgttcgagt    3840
gcattgagca cgccacctac gacacacttt cacacgctaa agaccagatc accgcccaaa    3900
tgcaagccct agacgaagaa gccgccctac tgccctaatg ggtgtttcat gggtgttttcc   3960
```

```
ctagtgtttc atggtgtttt cacctaagct agggaattgc gcgagaagtc tcgcaaaaat    4020
cagcaacccc cggaaccaca cagttcacgg gggttcttct atgccagaaa tcagaaaggg    4080
gaaccagtga acgaccccga atattggatc acagcgcagc aggtcgccgc ccgcgtagct    4140
ctcaccccgg ccaccattaa aaagtgggca aacgagggaa aaatcaccgc atacaagatc    4200
ggcaagtccg tccgattcaa agcatcagac gtagacaagc taggggggggg ggggcgctga    4260 ggtctgcctc gtgaagaagg tgttgctgac tcataccagg cctgaatcgc cccatcatcc    4320
agccagaaag tgagggagcc acggttgatg agagctttgt tgtaggtgga ccagttggtg    4380
attttgaact tttgctttgc cacggaacgg tctgcgttgt cgggaagatg cgtgatctga    4440
tccttcaact cagcaaaagt tcgatttatt caacaaagcc gccgtcccgt caagtcagcg    4500
taatgctctg ccagtgttac aaccaattaa ccaattctga ttagaagaac tcgtcaagaa    4560
ggcgatagaa ggcgatgcgc tgcgaatcgg gagcggcgat accgtaaagc acgaggaagc    4620
ggtcagccca ttcgccgcca agctcttcag caatatcacg ggtagccaac gctatgtcct    4680
gatagcggtc cgccacaccc agccggccac agtcgatgaa tccagaaaag cggccatttt    4740
ccaccatgat attcggcaag caggcatcgc catgggtcac gacgagatcc tcgccgtcgg    4800
gcatgctcgc cttgagcctg gcgaacagtt cggctggcgc gagcccctga tgctcttcgt    4860
ccagatcatc ctgatcgaca agaccggctt ccatccgagt acgtgctcgc tcgatgcgat    4920
gtttcgcttg gtggtcgaat gggcaggtag ccggatcaag cgtatgcagc cgccgcattg    4980
catcagccat gatggatact ttctcggcag gagcaaggtg agatgacagg agatcctgcc    5040
ccggcacttc gcccaatagc agccagtccc ttcccgcttc agtgacaacg tcgagcacag    5100
ctgcgcaagg aacgcccgtc gtggccagcc acgatagccg cgctgcctcg tcttgcagtt    5160
cattcagggc accggacagg tcggtcttga caaaagaac cgggcgcccc tgcgctgaca    5220
gccggaacac ggcggcatca gagcagccga ttgtctgttg tgcccagtca tagccgaata    5280
gcctctccac ccaagcggcc ggagaacctg cgtgcaatcc atcttgttca atcataacac    5340
cccttgtatt actgtttatg taagcagaca gttttattgt tcatgatgat atattttat     5400 cttgtgcaat gtaacatcag agattttgag acacaacgtg gctttccccc ccccccaaa     5460 aggatctagg tgaagatcct ttttgataat ctcatgacca aaatcccta acgtgagttt     5520 tcgttccact gagcgtcaga ccccgtagaa aagatcaaag gatcttc                   5567
```

SHUTTLE VECTORS FOR *CORYNEBACTERIUM* AND *ESCHERICHIA COLI*

CROSS-REFERENCE TO RELATED APPLICATIONS

This application claims the benefit of Korean Patent Application No. 10-2013-0008745, filed on 25 Jan. 2013, in the Korean Intellectual Property Office, the entire disclosure of which is incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 36,592 Bytes ASCII (Text) file named "713500_ST25.TXT," created on Jan. 22, 2014.

BACKGROUND

1. Field

The present disclosure relates to shuttle vectors for *Corynebacterium* and *Escherichia coli*, and promoter screening and gene product production using the same.

2. Description of the Related Art

*Corynebacterium* is a gram-positive bacterial strain widely used for the production of amino acids, such as glutamate, lysine, and threonine, and purine based nucleic acids, such as inosinic acid. *Corynebacterium glutamicum*, in particular, is easy to grow, tolerates high concentration cultivation (e.g., cultivation at concentrations up to approximately four times greater than concentrations tolerated by *Escherichia coli* (*E. coli*)), and has a stable genome that resists mutations. In addition, *Corynebacterium glutamicum* has several merits as an industrial strain, such as being a nonpathogenic strain, not forming spores, thus having no deleterious effects on the environment, and the like.

A cloning vector is a cyclic DNA which can be replicated independently from a main chromosome in bacteria. A cloning vector includes an origin of replication for maintenance of a plasmid form within the strain, a selectable marker gene for selection of strains having the cloning vector, and a multi-cloning site (MCS) for cloning an exogenous gene.

A shuttle vector generally includes a vector which is capable of being maintained in a plurality of strains. *Corynebacterium*-*E. coli* shuttle vectors include both an origin of replication of *Corynebacterium* and an origin of replication of *E. coli*. Use of shuttle vectors allows for easy introduction of a desired trait into a subject strain. For example, desired traits can be induced by cloning exogenous genes or mutation-inducing genes into a shuttle vector in *E. coli*, and then introducing the shuttle vector into *Corynebacterium*.

There is a need for shuttle vectors which are able to maintain and proliferate in both *Corynebacterium* and *E. coli*, and which allow for easy accomplishment of a variety of cloning by improving a multi-cloning site.

SUMMARY

Provided are vectors including a nucleotide sequence of SEQ ID NO: 1 and a multi-cloning site (MCS) sequence of SEQ ID NO: 2.

Provided are methods of examining promoter activity in *Corynebacterium* using the vectors.

Provided are methods of producing gene products from *Corynebacterium* using the vectors.

Provided are *E. coli* and *Corynebacterium* having the vectors.

Additional aspects will be set forth in part in the description which follows and, in part, will be apparent from the description, or may be learned by practice of the presented embodiments.

According to an aspect of the present invention, a vector includes a nucleotide sequence of SEQ ID NO: 1 and a MCS sequence of SEQ ID NO: 2. For example, the vector may have a nucleotide sequence of SEQ ID NO: 3. The nucleotide sequence of SEQ ID NO: 3 refers to nucleotide sequence of the entire pGSK+ vector in FIG. 2.

The vector contain a reporter gene and a transcription terminator operably linked in the MCS (e.g., operably linked by or to the MCS, such that sequences inserted at the MCS are operably linked to the reporter gene and transcription terminator). The term "operably linked" means that one nucleic acid fragment is linked to another nucleic acid fragment and the function or expression of the former is affected by the latter. The reporter gene and the transcription terminator may be linked such that expression of the reporter gene can be regulated by a promoter inserted into the MCS. Any reporter gene that allows for easy measurement of transcription-inducing activity of the promoter may be used for the reporter gene. For example, the reporter gene may be a chloramphenicol acetyltransferase (CAT) gene. The transcription terminator may be, for example, an intrinsic transcription terminator. The intrinsic transcription terminator may be, for example, a rrnB terminator. The vector may have, for example, a nucleotide sequence of SEQ ID NO: 4. The nucleotide sequence of SEQ ID NO: 4 refers to nucleotide sequence of the entire pGSP1 vector in FIG. 3.

The vector may be one in which a 3'-untranslated region (3'UTR) inducing gene expression stabilization, and a transcription terminator are operably linked in the MCS. The 3'UTR and the transcription terminator may be linked such that a gene of a promoter-gene inserted into the MCS can be stably expressed. The 3'UTR may be, for example, the 3'UTR of the *Corynebacterium* gltA gene. The transcription terminator may be, for example, an intrinsic transcription terminator. The intrinsic transcription terminator may be, for example, a rrnB terminator. The vector may have, for example, a nucleotide sequence of SEQ ID NO: 5. The nucleotide sequence of SEQ ID NO: 5 refers to nucleotide sequence of the entire pGT1 vector in FIG. 4.

The vector may contain a constitutive promoter, a 3'-untranslated region inducing gene expression stabilization, and a transcription terminator operably linked in the MCS. The "constitutive promoter" includes a promoter having a certain level of transcriptional activity regardless of growth conditions. The constitutive promoter may be, for example, *Corynebacterium glutamicum*-derived glyceraldehyde-3-phosphate dehydrogenase (gapA) (NCgl1526) gene promoter. The constitutive promoter may be, for example, one which is linked to a gene so that the gene inserted into the MCS can be expressed at a certain level regardless of the growth conditions of *Corynebacterium*. The 3'UTR and the transcription terminator may be, for example, linked such that the gene inserted into the MCS can be expressed. The 3'UTR may be, for example, the 3'UTR of the *Corynebacterium* citrate synthase (gltA) gene. The transcription terminator may be, for example, an intrinsic transcription terminator. The intrinsic transcription terminator may be, for example, a rrnB terminator. The vector may have, for example, the nucleotide sequence of SEQ ID NO: 6. The nucleotide sequence of SEQ ID NO: 6 refers to nucleotide sequence of the entire pGSX1 vector in FIG. 5.

According to another aspect of the present invention, a method of examining promoter activity includes: culturing a vector-introduced *Corynebacterium* in a medium, wherein the vector includes a nucleotide sequence of SEQ ID NO: 1 and a MCS sequence of SEQ ID NO: 2, and contains a reporter gene and a transcription terminator operably linked in the MCS, wherein a promoter is inserted into the MCS; measuring a product of the reporter gene; and examining the transcription-inducing activity of the promoter.

The culturing may be performed in any medium in which *Corynebacterium* can grow and proliferate. The promoter may be inserted into the MCS such that the reporter gene, which is operably linked to the promoter, is expressed. The promoter may be, for example, a promoter for testing the transcription-inducing activity in *Corynebacterium*. The transcription terminator may be, for example, an intrinsic transcription terminator. The intrinsic transcription terminator may be, for example, a rrnB terminator. The *Corynebacterium* may be, for example, *Corynebacterium glutamicum*. The reporter gene product may be, for example, chloramphenicol acetyltransferase.

For measuring the reporter gene product, a cytolysate of *Corynebacterium* may be obtained. Measuring the reporter gene product may be carried out, for example, by incubating the cytolysate of *Corynebacterium* containing a vector of the present invention, radioisotope-labelled chloramphenicol, and acetyl-CoA at 37° C. to produce radioisotope-labelled acetylchloramphenicol, and examining the radioisotope-labelled acetylchloramphenicol by chromatography and/or radioautography. The measuring also may be carried out by measuring the size of colonies formed on a chloramphenicol-containing medium.

The examining of transcription-inducing activity may be carried out, for example, by measuring acetylchloramphenicol produced, as compared to a control group. In this regard, the control group may be *Corynebacterium* containing a vector lacking a promoter insert cultured under identical conditions. The examining of transcription-inducing activity also may be carried out by examining whether larger colonies are formed or not, as compared to the control group. In this regard, the control group may be *Corynebacterium* containing a vector lacking a promoter insert cultured on a chloramphenicol-containing medium.

According to another aspect of the present invention, a method of producing a gene product from *Corynebacterium* includes: culturing a vector-introduced *Corynebacterium* in a medium, wherein the vector includes a nucleotide sequence of SEQ ID NO: 1 and a MCS sequence of SEQ ID NO: 2, and in which a constitutive promoter, a 3'UTR, and a transcription terminator are operably linked in the MCS, and in which a gene is inserted into the MCS; and separating a product of the gene from a result of the culturing.

The culturing may be performed in any medium in which *Corynebacterium* can grow and proliferate. The gene may be, for example, a gene for testing whether a gene product is produced in *Corynebacterium*. The gene may be, for example, one which is inserted into the MCS such that the expression of the gene is induced by the constitutive promoter. The constitutive promoter may be, for example, a *Corynebacterium glutamicum*-derived gapA gene promoter. The 3'UTR may be, for example, a 3'UTR of the *Corynebacterium* gltA gene. The transcription terminator may be, for example, an intrinsic transcription terminator. The intrinsic transcription terminator may be, for example, a rrnB terminator. The *Corynebacterium* may be, for example, *Corynebacterium glutamicum*.

The separating of a gene product may be carried out, for example, by harvesting a cultured cell, lysing the cell, and separating proteins from an obtained cell extract using common methods, such as chromatography, electrophoresis, etc. The separated gene product may undergo, for example, an additional purification process.

According to another aspect of the present invention, *E. coli* has a vector which includes the nucleotide sequence of SEQ ID NO: 1 and the MCS sequence of SEQ ID NO: 2. The *E. coli* may contain, for example, the nucleotide sequence of SEQ ID NO: 3. The *E. coli* may contain, for example, a vector which includes the nucleotide sequence of SEQ ID NO: 1 and the MCS sequence of SEQ ID NO: 2, wherein a reporter gene and a transcription terminator are operably linked in the MCS. The reporter gene and the transcription terminator may be, for example, linked such that the expression of the reporter gene can be regulated by a promoter inserted into the MCS. The reporter gene may be, for example, a chloramphenicol acetyltransferase gene. The *E. coli* may contain, for example, a vector which has the nucleotide sequence of SEQ ID NO: 4.

The *E. coli* may contain, for example, a vector which includes the nucleotide sequence of SEQ ID NO: 1 and the MCS sequence of SEQ ID NO: 2, wherein a 3'UTR and a transcription terminator are operably linked in the MCS. The 3'UTR and the transcription terminator are as described above. The 3'UTR and the transcription terminator may be, for example, linked such that the gene of the promoter-gene inserted into the MCS can be expressed. The *E. coli* may contain, for example, a vector which has the nucleotide sequence of SEQ ID NO: 5.

The *E. coli* may be used, for example, as a host cell for maintaining and proliferating the vector. A group of the host cells may constitute a genomic DNA library. The vector may include, for example, each fragment of the *Corynebacterium glutamicum* genome.

The *E. coli* may contain, for example, a vector which includes the nucleotide sequence of SEQ ID NO: 1 and the MCS sequence of SEQ ID NO: 2, wherein a constitutive promoter, a 3'UTR, and a transcription terminator are operably linked in the MCS. The constitutive promoter, the 3'UTR, and the transcription terminator are as described above. The constitutive promoter may be, for example, linked to the gene so that the gene inserted into the MCS can be expressed at a certain level regardless of the growth conditions of *Corynebacterium*. The 3'UTR and the transcription terminator may be, for example, linked such that the gene inserted into the MCS can be expressed. The *E. coli* may contain, for example, a vector which has the nucleotide sequence of SEQ ID NO: 6.

According to another aspect of the present invention, *Corynebacterium* has a vector which includes a nucleotide sequence of SEQ ID NO: 1 and a MCS sequence of SEQ ID NO: 2. The *Corynebacterium* may contain, for example, a nucleotide sequence of SEQ ID NO: 3.

The *Corynebacterium* may contain, for example, a vector which includes the nucleotide sequence of SEQ ID NO: 1 and the MCS sequence of SEQ ID NO: 2, wherein a reporter gene and a transcription terminator are operably linked in the MCS. The reporter gene and the transcription terminator may be, for example, linked such that expression of the reporter gene can be regulated by a promoter inserted into the MCS. The reporter gene may be, for example, chloramphenicol acetyltransferase gene. The *Corynebacterium* may contain, for example, a vector which has a nucleotide sequence of SEQ ID NO: 4.

The *Corynebacterium* may contain, for example, a vector which includes the nucleotide sequence of SEQ ID NO: 1 and the MCS sequence of SEQ ID NO: 2, wherein a 3'UTR and a transcription terminator are operably linked in the MCS. The 3'UTR and the transcription terminator are as described above. The 3'UTR and the transcription terminator may be, for example, linked such that a gene of a promoter-gene inserted into the MCS can be expressed. The *Corynebacterium* may contain, for example, a vector which has a nucleotide sequence of SEQ ID NO: 5.

The *Corynebacterium* may contain, for example, a vector which includes the nucleotide sequence of SEQ ID NO: 1 and the MCS sequence of SEQ ID NO: 2, wherein a constitutive promoter, a 3'UTR, and a transcription terminator are operably linked in the MCS. The constitutive promoter, the 3'UTR, and the transcription terminator are as described above. The constitutive promoter may be, for example, linked to a gene so that the gene inserted into the MCS can be expressed at a certain level regardless of the growth conditions of *Corynebacterium*. The 3'UTR and the transcription terminator may be, for example, linked such that the gene inserted into the MCS can be expressed. The *Corynebacterium* may contain, for example, a vector which has a nucleotide sequence of SEQ ID NO: 6. The *Corynebacterium* may be used, for example, as a host cell which overexpresses the gene inserted in the vector.

The *Corynebacterium* may be, for example, *Corynebacterium glutamicum*.

According to one embodiment, the shuttle vector of the present invention can be used for gene cloning, gene or promoter screening, gene product production, and genomic DNA library manufacture in *Corynebacterium*.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
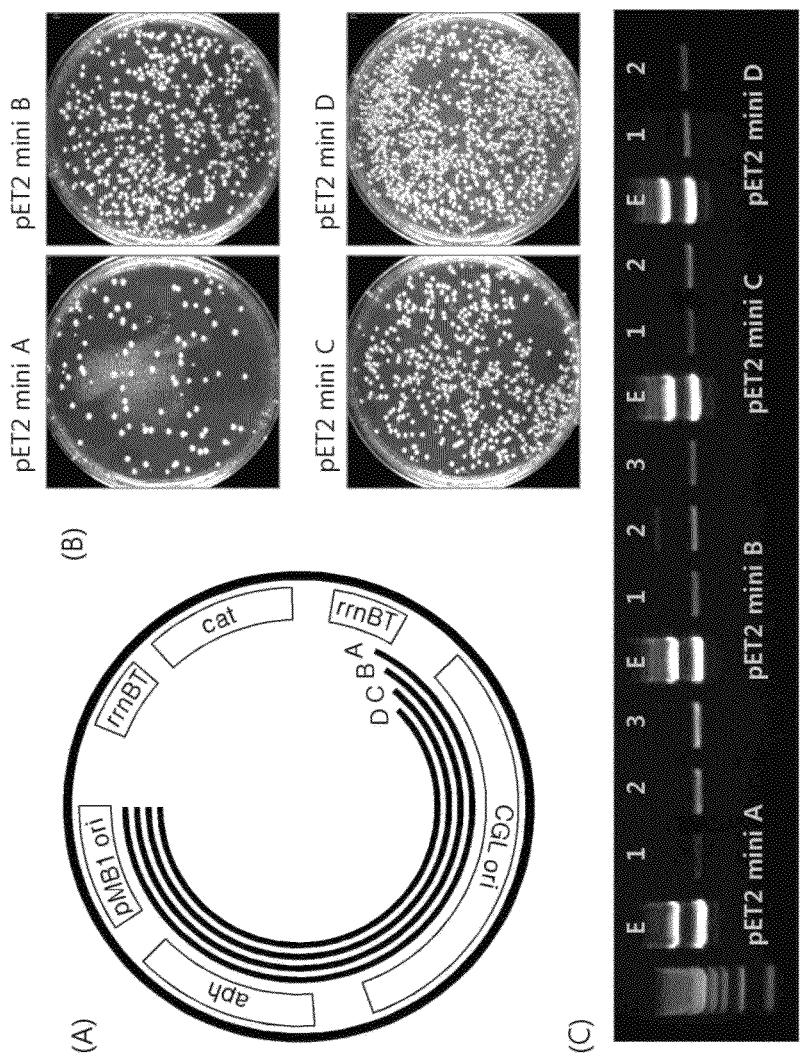
FIG. 1 is a map, photographs, and a gel image showing that four pET2 mini vectors manufactured by serial deletion are maintained and replicated in *Corynebacterium glutamicum;*

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

Example 1

Manufacture of pET2 Mini Vector through Serial Deletion

A mini vector made up of the site represented by A (pET2 mini A, 4911 bp), a mini vector made up of the site represented by B (pET2 mini B, 4818 bp), a mini vector made up of the site represented by C (pET2 mini C, 4717 bp), and a mini vector made up of the site represented by D (pET2 mini D, 4647 bp) were manufactured from a *E. coli-Corynebacterium glutamicum* shuttle vector, pET2 (GenBank accession number: AJ885178.1, 7513 bp).

FIG. 1 is an experimental result showing that four pET2 mini vectors manufactured by serial deletion are maintained and replicated in *Corynebacterium glutamicum*. FIG. 1(A) shows a site of independent mini vectors manufactured from pET2 vector. FIG. 1(B) shows that when pET2 mini D, whose size was reduced by about 270 bp as compared to pET2 mini A, was transformed in *Corynebacterium glutamicum*, a larger number of colonies were obtained. FIG. 1(C) shows a result confirming that each mini vector was maintained in a form of plasmid in both *E. coli* and *Corynebacterium glutamicum*. Lane E confirms that the plasmid was separated from *E. coli*. Lanes 1 to 3 confirm that the plasmids were separated from *Corynebacterium glutamicum*.

Example 2 pGSK+, Shuttle Vector for Cloning *E. coli-Corynebacterium qlutamicum*

Based on pET2 mini D in Example 1, a pET2-derived kanamycin-resistance gene, aph gene, was substituted with a Tn5-derived kanamycin-resistance gene, neo gene (nptII), to remove a restriction enzyme recognition site. In addition, an XbaI restriction enzyme recognition site in the rep gene was removed by point mutation. Then, the MCS derived from pBluescriptII SK(+) phagemid vector, which has 14 restriction enzyme recognition sites, was inserted to manufacture a shuttle vector for cloning *E. coli-Corynebacterium glutamicum*, pGSK+.

Figure 2:
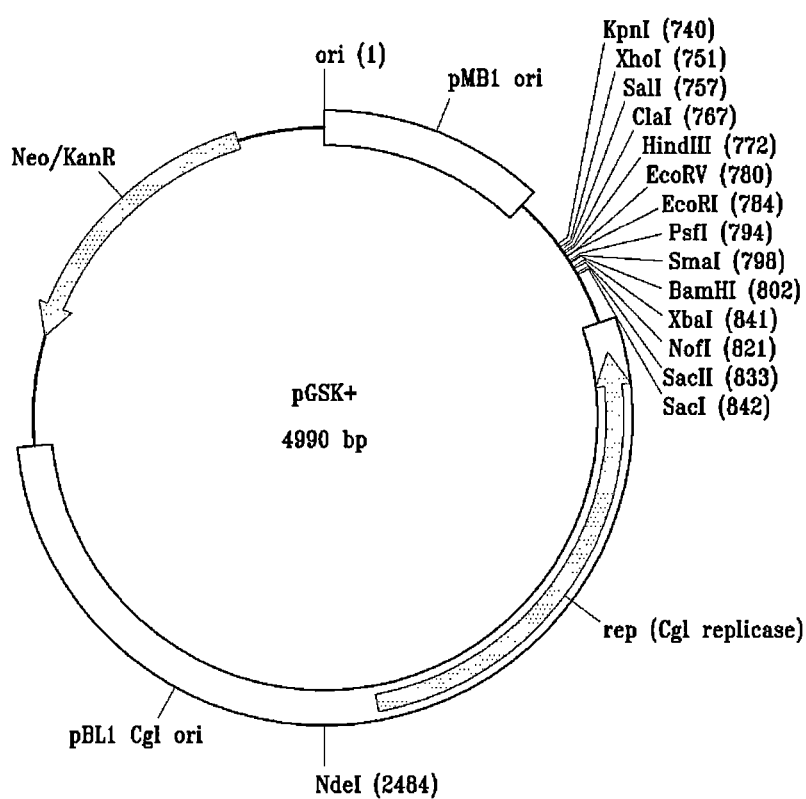
FIG. 2 is a map of pGSK+, a shuttle vector for gene cloning.

FIG. 2 shows a map of pGSK+, the shuttle vector for gene cloning. It shows a genetic organization along with restriction enzyme recognition sites. Arrows refer to open reading frames (ORFs) and the directions of arrows refer to the direction of transcription. pMB1 on refers to a replication origin for replication in *E. coli*, and pBL1 cgl on refers to a replication origin for replication in *Corynebacterium glutamicum*, and its portion, rep, refers to a CgI replicase gene.

Example 3 pGPS1, Shuttle Vector for Promoter Screening

Based on pGSK+ in Example 2, a pET2-derived chloramphenicol acetyltransferase (CAT) gene-rrnB terminator was inserted between ClaI and SacI in a MCS to manufacture a shuttle vector for promoter screening, pGPS1.

Figure 3:
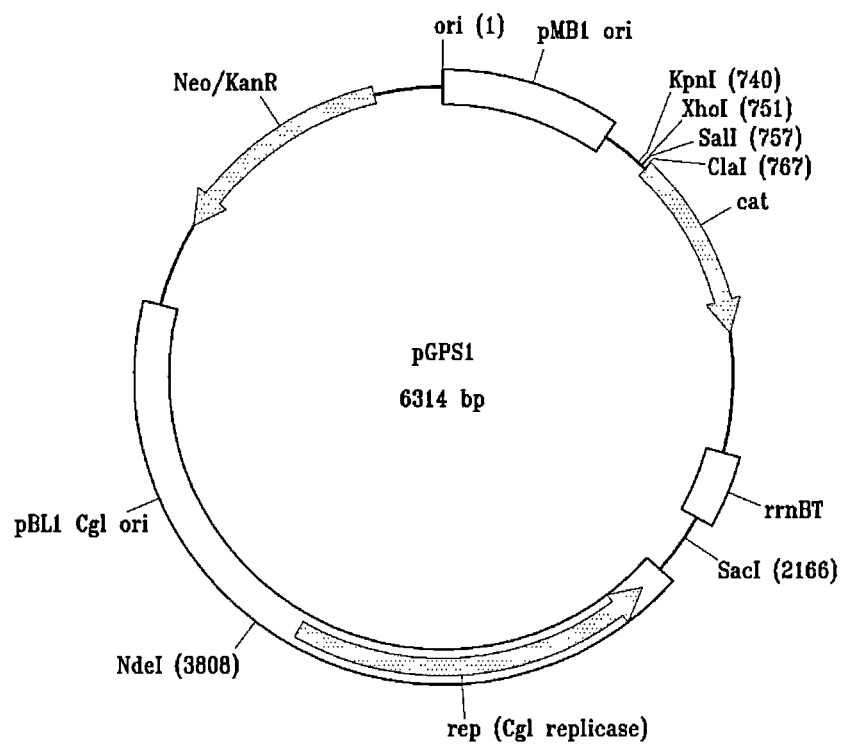
FIG. 3 is a map of pGPS1, a shuttle vector for promoter screening.

FIG. 3 shows a map of pGPS1, the shuttle vector for promoter screening. It shows a genetic organization along with restriction enzyme recognition sites. Arrows refer to ORFs and the directions of arrows refer to the direction of transcription. pMB1 ori, pBL1 CgI ori, and rep are as described in Example 2. cat refers to the chloramphenicol acetyltransferase gene, and rrnBT refers to a rrnB terminator.

Example 4 pGT1, Shuttle Vector for Promoter-exogenous Gene Cloning

Based on pGSK+ in Example 2, the 3'UTR (untranslated region) of the gltA gene and rrnB terminator were inserted into the SalI position of pGSK+ to manufacture a shuttle vector for promoter-exogenous gene cloning, pGT1.

Figure 4:
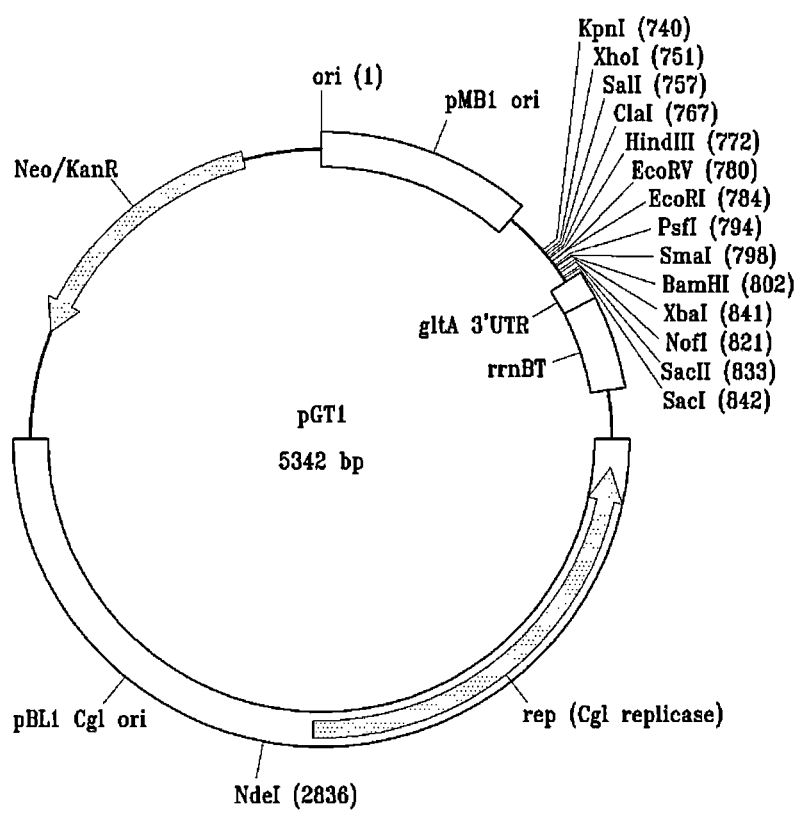
FIG. 4 is a map of pGT1, a shuttle vector for promoter-gene cloning.

FIG. 4 shows a map of pGT1, the shuttle vector for promoter-gene cloning. It shows a genetic organization along with restriction enzyme recognition sites. Arrows refer to ORFs and the directions of arrows refer to the direction of transcription. pMB1 ori, pBL1 CgI ori, rep, and cat are as described in Example 2 and Example 3.

Example 5 pGSX1, Shuttle Vector for Overexpression

Based on pGT1 in Example 4, a promoter of *Corynebacterium glutamicum*-derived gapA gene was inserted between KpnI and XhoI in the MCS to manufacture a shuttle vector for exogenous gene overexpression, pGSX1.

Figure 5:
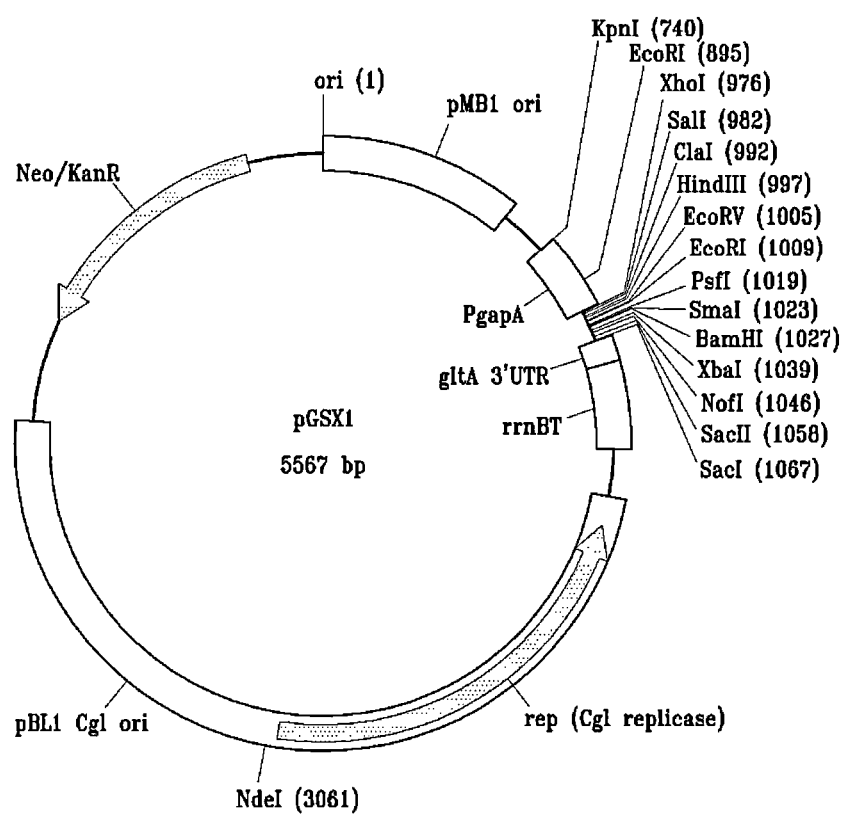
FIG. 5 is a map of pGSX1, a shuttle vector for exogenous gene overexpression.

FIG. 5 shows a map of pGSX1, the shuttle vector for exogenous gene overexpression. It shows a genetic organization along with restriction enzyme recognition sites. Arrows refer to ORFs and the directions of arrows refer to the direction of transcription. pMB1 ori, pBL1 CgI ori, rep, and cat are as described in Example 2 and Example 3. PgapA refers to the promoter of a gapA gene.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A vector comprising a nucleotide sequence of SEQ ID NO: 1 and a multi-cloning site (MCS) comprising a nucleotide sequence of SEQ ID NO: 2.

2. The vector of claim 1, wherein the vector comprises a nucleotide sequence of SEQ ID NO: 3.

3. A vector comprising a nucleotide sequence of SEQ ID NO: 1 and a multi-cloning site (MCS) comprising a nucleotide sequence of SEQ ID NO: 2 into which a reporter gene and a transcription terminator, a 3'untranslated region (3'UTR) and a transcription terminator, or a constitutive promoter, a 3'UTR, and a transcription terminator, have been inserted and operably linked.

4. The vector of claim 3, wherein the reporter gene is a chloramphenicol acetyltransferase (CAT) gene.

5. The vector of claim 4, wherein the vector comprises a nucleotide sequence of SEQ ID NO: 4.

6. The vector of claim 3, wherein the vector comprises a nucleotide sequence of SEQ ID NO: 5.

7. The vector of claim 3, wherein the vector comprises a nucleotide sequence of SEQ ID NO: 6.

8. A method of examining promoter activity, the method comprising:
culturing a *Corynebacterium* comprising a vector in a medium, wherein the vector comprises a nucleotide sequence of SEQ ID NO: 1, a MCS sequence of SEQ ID NO: 2 into which a promoter, a reporter gene, and a transcription terminator have been inserted and operably linked, whereby a product of the reporter gene is expressed;
measuring the product of the reporter gene; and
examining the transcription-inducing activity of the promoter based on the measurement.

9. A method of producing a gene product in *Corynebacterium*, the method comprising:
culturing a *Corynebacterium* comprising a vector in a medium, wherein the vector comprises a nucleotide sequence of SEQ ID NO: 1 and a MCS sequence of SEQ ID NO: 2 into which a gene, a constitutive promoter, a 3'UTR, and a transcription terminator have been inserted and operably linked, whereby a gene product of the gene is produced.

10. The method of claim 9, further comprising separating the gene product from the medium.

11. The method of claim 8, wherein the *Corynebacterium* is *Corynebacterium glutamicum*.

12. The method of claim 9, wherein the *Corynebacterium* is *Corynebacterium glutamicum*.

13. An *E. coli* comprising the vector of claim 1.

14. A *Corynebacterium* comprising the vector of claim 1.

* * * * *